United States Patent

Tarumi et al.

Patent Number: 5,965,060
Date of Patent: Oct. 12, 1999

[54] ELECTRO-OPTICAL LIQUID CRYSTAL DISPLAY

[75] Inventors: Kazuaki Tarumi, Seeheim; Brigitte Schuler, Grossostheim; Matthias Bremer, Darmstadt, all of Germany

[73] Assignee: Merck Patent Gesellschaft mit Beschrankter Haftung, Germany

[21] Appl. No.: 08/989,771

[22] Filed: Dec. 12, 1997

[30] Foreign Application Priority Data

Dec. 13, 1996 [DE] Germany ............................ 196 51 885

[51] Int. Cl.⁶ .......................... C09K 19/30; C09K 19/34; G02F 1/1333
[52] U.S. Cl. .............................. 252/299.63; 252/299.61; 252/299.66; 349/99; 349/123; 349/130; 349/181
[58] Field of Search ........................ 252/299.61, 299.63, 252/299.66, 299.67; 349/123, 99, 130, 181

[56] References Cited

U.S. PATENT DOCUMENTS

| 4,130,502 | 12/1978 | Eidenschink et al. | 252/299.01 |
| 4,330,426 | 5/1982 | Eidenschink et al. | 252/299.63 |
| 4,622,164 | 11/1986 | Eidenschink et al. | 252/299.63 |
| 5,384,065 | 1/1995 | Geelhaar et al. | 252/299.63 |
| 5,599,480 | 2/1997 | Tarumi et al. | 252/299.63 |

FOREIGN PATENT DOCUMENTS 8-104869   4/1996   Japan .

OTHER PUBLICATIONS

Derwent Abstract of DE 4 444 813 A.
Derwent Abstract of DE 38 078 72 A.

*Primary Examiner*—Shean C. Wu
*Attorney, Agent, or Firm*—Millen, White, Zelano & Branigan, P.C.

[57] ABSTRACT

An electro-optical liquid crystal display with active-matrix addressing, in which the liquid-crystal layer has a homeotropic or tilted homeotropic alignment in the switched-off state and which contains a liquid-crystalline medium of negative dielectric anisotropy. The medium contains A) 30–70% by weight of two or more compounds of the formula I

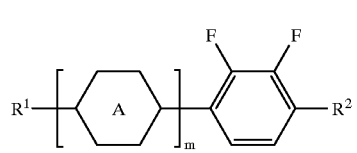

and B) 20–50% by weight of two or more compounds of the formula II

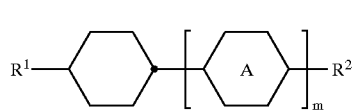

in which $R^1$, $R^2$,

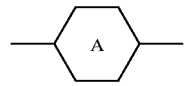

and m are as defined in claim 1. The displays are particularly capable of operation based on the vertically-aligned cholesteric or nematic (VAC or VAN) effect.

12 Claims, No Drawings

ELECTRO-OPTICAL LIQUID CRYSTAL DISPLAY

The invention relates to an electro-optical liquid-crystal display with active-matrix addressing, in which the liquid-crystal layer has a homeotropic or tilted homeotropic alignment in the switched-off state and which contains a liquid-crystalline medium of negative dielectric anisotropy, characterized in that the medium essentially consists of A) 30–70% by weight of two or more compounds of the formula I

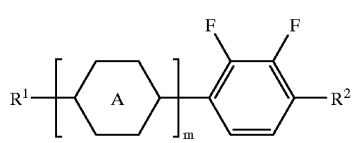

in which

R$^1$ and R$^2$ are each, independently of one another, an alkyl or alkenyl radical having 1 to 15 carbon atoms which is unsubstituted, monosubstituted by CN or CF$_3$ or monosubstituted to perhalo-substituted by halogen, where, in addition, one or more CH$_2$ groups in these radicals may each, independently of one another, be replaced by —O—, —S—, —CO—, —CO—O—, —O—CO— or —OCO—O— in such a way that —O— atoms are not linked to one another,

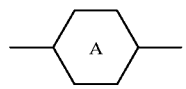

is a trans-1,4-cyclohexylene radical, in which, in addition, one or more non-adjacent CH$_2$ groups may be replaced by —O— and/or —S—, or a 1,4-phenylene radical, in which, in addition, one or two CH groups may be replaced by —N—, and m is 1, 2 or 3, and B) 20–50% by weight of two or more compounds of the formula II

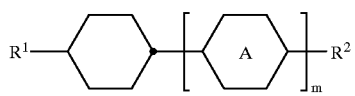

in which R$^1$, R$^2$,

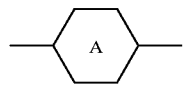

and m are as defined for the formula I.

The invention furthermore relates to liquid-crystal displays containing a liquid-crystalline medium as described above, characterized in that these liquid-crystal displays are operated with active-matrix addressing based on the VAN (vertically aligned nematic) effect or the VAC (vertically aligned cholesteric) effect.

The invention also relates to liquid-crystalline media for the liquid-crystal displays described above.

BACKGROUND OF THE INVENTION

Liquid-crystal displays with active-matrix addressing in which the liquid-crystal layer has a homeotropic or tilted homeotropic alignment in the switched-off state, such as, for example, displays based on the ECB (electrically controlled birefringence) effect or the DAP (deformation of aligned phases) effect, are known. They were described for the first time in M. F. Schiekkel and K. Fahrenschon, Appl. Phys. Lett. 19, 3912 (1971).

However, liquid-crystal displays of this type have some disadvantages compared with known active-matrix TN displays, in particular a high viewing-angle dependence of the contrast and of the grey shades.

A newer variant of ECB displays is active-matrix displays based on the VAN (vertically aligned nematic) effect or the VAC (vertically aligned cholesteric) effect. VAN displays have been described, inter alia, in S. Yamauchi et al., SID Digest of Technical Papers, pp. 378ff (1989), and VAC displays have been described in K. A. Crabdall et al., Appl. Phys. Lett. 65, 4 (1994).

Like the ECB displays which were known earlier, the more-recent VAN and VAC displays contain a layer of liquid-crystalline medium between two transparent electrodes, where the liquid-crystalline medium has a negative value for the anisotropy of the dielectric constants Δε. The molecules in this liquid-crystal layer have a homeotropic or tilted homeotropic alignment in the switched-off state, i.e. are aligned substantially perpendicular to the electrode surfaces. Owing to the negative Δε, realignment of liquid-crystal molecules parallel to the electrode surface takes place in the switched-on state.

In contrast to conventional ECB displays, in which the liquid-crystal molecules in the switched-on state have a parallel alignment with a uniform preferential direction over the entire liquid-crystal cell, this uniform parallel alignment in VAN and VAC displays is restricted only to small domains within the cell. Disclinations exist between these domains, which are also known as tilt domains.

As a consequence, VAN and VAC displays have a greater viewing-angle independence of the contrast and of the grey shades than conventional ECB displays. In addition, such displays are simpler to produce, since additional treatment of the electrode surface, such as, for example, by rubbing, for uniform alignment of the molecules is no longer necessary.

In contrast to VAN displays, the liquid-crystal media in VAC displays additionally comprise one or more chiral compounds, such as, for example, chiral dopants, which, in the switched-on state, produce a helical twist of the liquid-crystal molecules in the liquid-crystal layer by an angle of between 0 and 360°. The twist angle in the preferred case is about 90°.

In particular for these novel VAN and VAC displays, special customized liquid-crystal media are required. For example, it has been found that the liquid-crystalline media of negative dielectric anisotropy disclosed hitherto, as described, for example, in EP 0 474 062, have low values for the voltage holding ratio (HR) after UV exposure. They are therefore not very suitable for use in the displays described above.

SUMMARY OF THE INVENTION

Thus, there continues to be a great demand for liquid-crystal displays with active-matrix addressing in which the liquid-crystal layer has a homeotropic or tilted homeotropic alignment in the switched-off state, and which do not have the above-described disadvantages of ECB displays, or only do so to a small extent, and contain a suitable liquid-crystalline medium of negative dielectric anisotropy. The liquid-crystalline medium should have a high value for the voltage holding ratio and low viscosity values, in particular rotational viscosity values.

The object of the invention is to provide liquid-crystal media for active-matrix displays of this type.

It has now been found that this object can be achieved by using liquid-crystal media which essentially consist of A) 30–70% by weight of two or more compounds of the formula I

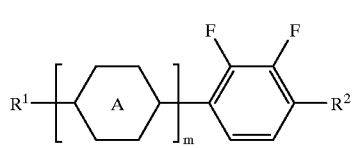

and

B) 20–50% by weight of two or more compounds of the formula II

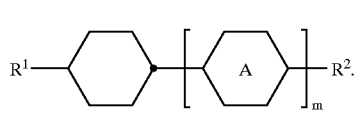

Compounds of this type are disclosed, for example, in DE 44 44 813 A1, which describes liquid-crystalline media of negative dielectric anisotropy for conventional ECB displays. However, there is no mention therein of VAN or VAC displays.

The invention thus relates to an electro-optical liquid-crystal display with active-matrix addressing, in which the liquid-crystal layer has a homeotropic or tilted homeotropic alignment in the switched-off state and which contains a liquid-crystalline medium of negative dielectric anisotropy, characterized in that the medium essentially consists of A) 30–70% by weight of two or more compounds of the formula I

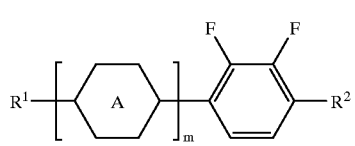

in which
R$^1$ and R$^2$ are each, independently of one another, an alkyl or alkenyl radical having 1 to 15 carbon atoms which is unsubstituted, monosubstituted by CN or CF$_3$ or monosubstituted to perhalo-substituted by halogen, where, in addition, one or more CH$_2$ groups in these radicals may each, independently of one another, be replaced by —O—, —S—, —CO—, —CO—O—, —O—CO— or —OCO—O in such a way that —O— atoms are not linked to one another.

is a trans-1,4-cyclohexylene radical, in which, in addition, one or more non-adjacent CH$_2$ groups may be replaced by —O— and/or —S—, or a 1,4-phenylene radical, in which, in addition, one or two CH groups may be replaced by —N—, and m is 1, 2 or 3, and B) 20–50% by weight of two or more compounds of the formula II

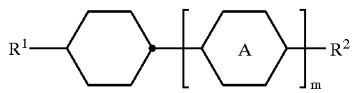

in which R$^1$, R$^2$,

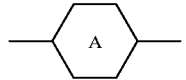

and m are as defined for the formula I.

Upon further study of the specification and appended claims, further objects and advantages of this invention will become apparent to those skilled in the art.

Preferred embodiments of the invention are a) a liquid-crystal display in which the liquid-crystalline medium comprises at least two compounds selected from the formulae Ia and Ib

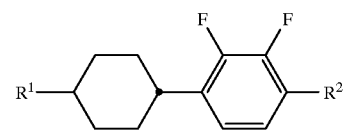

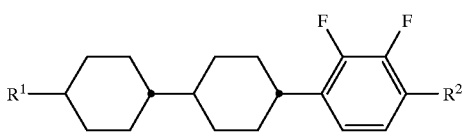

in which R$^1$ and R$^2$ are as defined for the formula I;

b) a liquid-crystal display in which the liquid-crystalline medium comprises at least two compounds selected from the formulae IIa to IIc

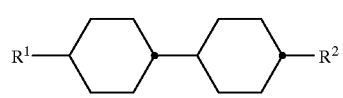

-continued

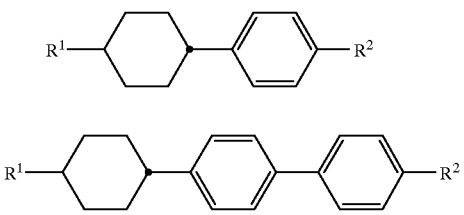

in which $R^1$ and $R^2$ are as defined for the formula I;
c) a liquid-crystal display in which the liquid-crystalline medium additionally comprises one or more compounds of the formula III

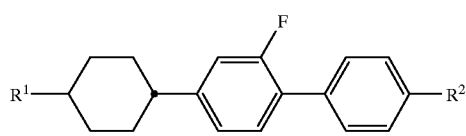

in which $R^1$ and $R^2$ are as defined for the formula I;
d) a liquid-crystal display in which the liquid-crystalline medium additionally comprises one or more compounds of the formula IV

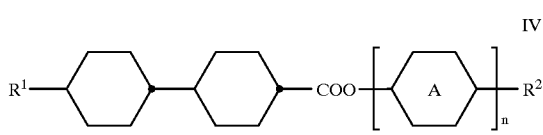

in which $R^1$, $R^2$ and

are as defined for the formula I, and n is 1 or 2;
e) a liquid-crystal display which is operated with active-matrix addressing based on the VAN (vertically aligned nematic) effect;
f) a liquid-crystal display which is operated with active-matrix addressing based on the VAC (vertically aligned cholesteric) effect.

The invention furthermore relates to the liquid-crystalline medium used in such displays.

The liquid-crystalline media present in the novel liquid-crystal displays generally have a nematic phase range of at least 60° K and a dielectric anisotropy Δε of from −0.5 to −5, in particular from −2 to −4.5. The birefringence is generally from 0.04 to 0.15, in particular from 0.06 to 0.12. The rotational viscosity is generally a maximum of 160 mPa·s.

The liquid-crystalline media present in the novel liquid-crystal displays preferably comprise
one to five, preferably two or three, compounds of the formula Ia,
one to five, preferably two or three, compounds of the formula Ib,
two to ten, preferably three to eight, compounds selected from the formulae IIa, IIb and IIc.

Preference is furthermore given to novel liquid-crystal displays containing liquid-crystalline media which additionally comprise
one to four, preferably two to three compounds of the formula III
and/or
one or more, preferably two to four, compounds of the formula IV.

The proportion of the compounds of the formula III or IV in the media in these preferred liquid-crystal displays is particularly preferably from 10 to 25% by weight.

In the compounds of the formula IV, n is preferably 1. Furthermore,

in the compounds of the formula IV is preferably trans-1, 4-cyclohexylene or 1,4-phenylene, particularly preferably trans-1,4-cyclohexylene.

In a further preferred embodiment, the novel liquid-crystal displays contain liquid-crystalline media which essentially consist of
A) 30–70% by weight, preferably 40–60% by weight, of two or more compounds of the formula I, and
B) 20–50% by weight, preferably 25–40% by weight, of two or more compounds of the formula II.

Particular preference is given to liquid-crystal displays containing liquid-crystalline media which essentially consist of
A1) 15–30% by weight of two or three compounds of the formula Ia,
A2) 25–40% by weight of two or three compounds of the formula Ib, and
B) 25–40% by weight of three to eight compounds selected from the formulae IIa to IIc.

In the compounds of the formulae I to IV, $R^1$ and $R^2$ are preferably, independently of one another, alkyl, alkoxy, alkenyl, fluoroalkyl or oxaalkyl having 1 to 12 carbon atoms.

The compounds of the formulae I to IV are colorless, stable and readily miscible with one another and with other liquid-crystal materials.

The term "alkyl" particularly preferably covers straight-chain and branched alkyl groups having 1–7 carbon atoms, in particular the straight-chain groups methyl, ethyl, propyl, butyl, pentyl, hexyl and heptyl. Groups having 2–5 carbon atoms are generally preferred.

The term "alkenyl" particularly preferably covers straight-chain and branched alkenyl groups having 2–7 carbon atoms, in particular the straight-chain groups. Particular alkenyl groups are $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, in particular $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having 2 to 5 carbon atoms are generally preferred for alkyl groups.

The term "fluoroalkyl" particularly preferably covers straight-chain groups having a terminal fluorine atom, i.e. fluoromethyl, 2-fluoroethyl, 3-fluoropropyl, 4-fluorobutyl, 5-fluoropentyl, 6-fluorohexyl and 7-fluoroheptyl. However, other positions of the fluorine are not excluded.

The term "oxaalkyl" particularly preferably covers straight-chain radicals of the formula $C_n H_{2n+1}-O-(CH_2)_m-$, in which n and m are each, independently of one another, from 1 to 6. Preferably, n=1 and m is from 1 to 6.

Through a suitable choice of the meanings of $R^1$ and $R^2$, the response times, the threshold voltage and the steepness of the transmission characteristic lines of the novel liquid-crystal display, can be modified as desired. For example, 1E-alkenyl radicals, 3E-alkenyl radicals, 2E-alkenyloxy radicals and the like generally result in shorter response times, improved nematic tendencies and a higher ratio between the elastic constants $k_{33}$ (bend) and $k_{11}$ (splay) compared with alkyl and alkoxy radicals. 4-Alkenyl radicals, 3-alkenyl radicals and the like generally result in lower threshold voltages and smaller values of $k_{33}/k_{11}$ compared with alkyl and alkoxy radicals.

The optimum mixing ratio between the compounds of the formulae I and II depends substantially on the desired properties, on the choice of the components of the formulae I and/or II and on the choice of any other components present. Suitable mixing ratios within the abovementioned range can easily be determined from case to case.

In addition to compounds of the formulae I and II, the mixtures may contain one or more further components in order to optimize various properties.

The novel liquid-crystalline media preferably comprise 2 to 40, in particular 4 to 30, components as further constituents besides one or more compounds of the formulae I, II, III and IV. These media very particularly preferably comprise 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes optionally halogenated stilbenes, benzyl phenyl ethers, tolans and substituted cinnamic acids. The 1,4-phenylene groups in these compounds may also be fluorinated.

The most important compounds suitable as further constituents of novel media can be characterized by the formulae 1, 2, 3, 4 and 5:

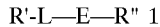 1

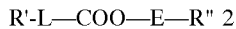 2

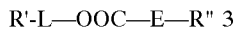 3

 4

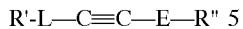 5

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The novel media preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller sub-group of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller sub-group is called group A below, and the compounds are labelled with the sub-formulae 1a, 2a, 3a, 4a and 5a. In most of these compounds, R' and R" are different from one another, one of these radicals usually being alkyl, alkenyl, alkoxy or alkoxyalkyl.

In another smaller sub-group of the compounds of the formulae 1, 2, 3, 4 and 5, which is known as group B, R" is $-F$, $-Cl$, $-NCS$ or $-(O)_iCH_{3-(k+1)}F_kCl_1$, where i is 0 or 1, and k+l is 1, 2 or 3; the compounds in which R" has this meaning are labelled with the sub-formulae 1b, 2b, 3b, 4b and 5b. Particular preference is given to those compounds of the sub-formulae 1b, 2b, 3b, 4b and 5b in which R" is $-F$, $-Cl$, $-NCS$, $-CF_3$, $-OCHF_2$ or $-OCF_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R" is $-CN$; this sub-group is known as group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formulae I and II according to the invention, the novel media preferably contain one or more compounds selected from group A and/or group B and/or group C. The proportions by weight of the compounds from these groups in the novel media are preferably Group A: 0 to 50%, preferably 5 to 40%, in particular 5 to 30%

Group B: 0 to 40%, preferably 5 to 35%, in particular 5 to 30%

Group C: 0 to 30%, preferably 5 to 25%, in particular 5 to 20%, the sum of the proportions by weight of the group A and/or B and/or C compounds present in the particular novel media preferably being 5% to 60% and in particular 5% to 40%.

The liquid-crystal mixtures which can be used in accordance with the invention are prepared in a manner conventional per se. In general, the desired amount of the components used in lesser amount is dissolved in the component making up the principal constituent, expediently at elevated temperature. It is also possible to mix solutions of the components in an organic solvent, for example in acetone, chloroform or methanol, and, after mixing, to remove the solvent again, for example by distillation.

The liquid-crystal media may also contain further additives known to the person skilled in the art and described in the literature. For example, 0–15% of pleochroic dyes or chiral dopants can be added.

The individual components of the formulae I to IV in the liquid-crystal media of the novel liquid-crystal displays are either known or their methods of preparation can readily be derived by the person skilled in the relevant art from the prior art, since they are based on the standard methods described in the literature.

Corresponding compounds of the formula I are described, for example, in WO 89/08633. Corresponding compounds of the formula II are described, for example, in DE 26 36 684, DE 29 27 277 or DE 33 21 373.

In the foregoing and in the following examples, all temperatures are set forth uncorrected in degrees Celsius; and, unless otherwise indicated, all parts and percentages are by weight.

The entire disclosure of all applications, patents and publications, cited above and below, and of corresponding German application No. 196 51 885.7, filed Dec. 13, 1996 is hereby incorporated by reference.

EXAMPLES

The examples below are intended to illustrate the invention without representing a limitation. Unless otherwise stated, all percentages above and below are percent by weight, all temperatures are given in degrees Celsius. An denotes the optical anisotropy and $n_o$, denotes the ordinary refractive index (in each case at 589 nm and 20° C.). $\Delta\epsilon$ denotes the dielectric anisotropy and $\epsilon_\perp$ denotes the dielectric constant perpendicular to the longitudinal molecular axis.

The following abbreviations are used:

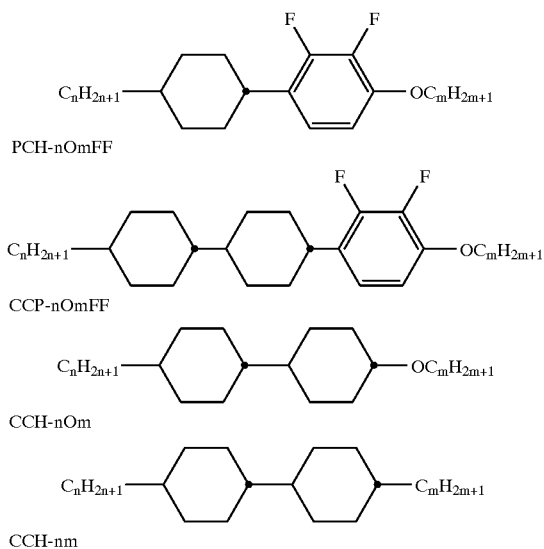

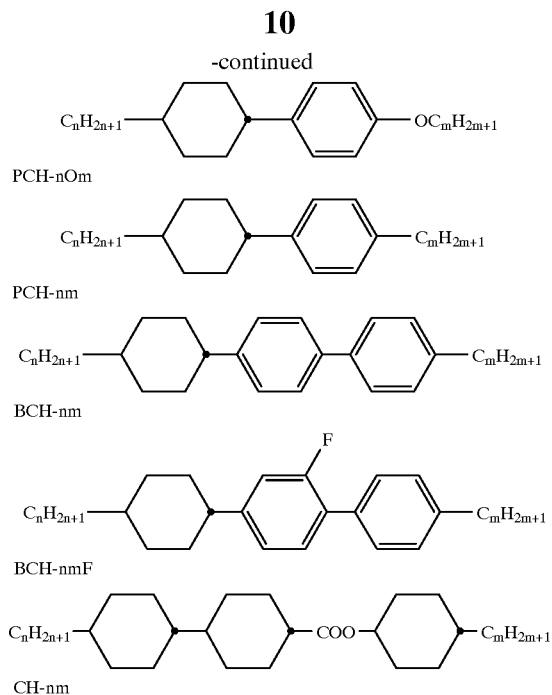

Example 1

A mixture is prepared which consists of

| Compound | % |
|---|---|
| PCH-302FF | 12.00 |
| PCH-502FF | 11.00 |
| CCP-302FF | 15.00 |
| CCP-502FF | 15.00 |
| CH-33 | 5.00 |
| CH-35 | 6.00 |
| CH-43 | 6.00 |
| CCH-34 | 5.00 |
| CCH-35 | 5.00 |
| CCH-301 | 6.00 |
| CCH-303 | 6.00 |
| PCH-301 | 4.00 |
| PCH-32 | 4.00 |

The mixture has the following properties:

| Clearing point | 92° C. |
|---|---|
| $\Delta n$ | 0.0759 |
| $n_o$ | 1.4747 |
| $\Delta\epsilon$ | −3.6 |
| $\epsilon_\perp$ | 7.0 |

Example 2

A mixture is prepared which consists of

| Compound | % |
|---|---|
| PCH-302FF | 10.00 |
| PCH-502FF | 10.00 |
| CCP-302FF | 9.00 |
| CCP-502FF | 7.00 |
| CCP-21FF | 8.00 |

-continued

| Compound | % |
|---|---|
| CCP-31FF | 8.00 |
| BCH-32 | 6.00 |
| BCH-52 | 5.00 |
| BCH-32F | 7.00 |
| BCH-52F | 7.00 |
| PCH-301 | 8.00 |
| PCH-32 | 15.00 |

The mixture has the following properties:

| Clearing point | 82° C. |
|---|---|
| $\Delta n$ | 0.1106 |
| $n_o$ | 1.4902 |
| $\Delta \epsilon$ | -2.6 |
| $\epsilon_\perp$ | 6.1 |

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. An electro-optical liquid-crystal display with active-matrix addressing, which is capable of operation by active-matrix addressing based on the vertically aligned cholesteric effect or the vertically aligned nematic effect, having a liquid-crystal layer with a homeotropic or tilted homeotropic alignment in the switched-off state and containing a liquid-crystalline medium of negative dielectric anisotropy, wherein the medium consists essentially of:

A) 30–70% by weight of two or more compounds of the formula I

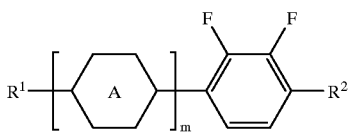

I in which $R^1$ and $R^2$ are each, independently of one another, an alkyl or alkenyl radical having 1 to 15 carbon atoms which is unsubstituted, monosubstituted by CN or $CF_3$ or monosubstituted to perhalo-substituted by halogen, where, in addition, one or more $CH_2$ groups in these radicals are optionally independently of one another, replaced by —O—, —S—, —CO—, —CO—O—, —O—CO— or —OCO—O in such a way that —O— atoms are not linked to one another,

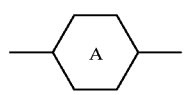

is a trans-1,4-cyclohexylene radical, in which one or more non-adjacent $CH_2$ groups are optionally replaced by —O— and/or —S—, or a 1,4-phenylene radical, in which one or two CH groups are optionally replaced by —N—, and m is 1, 2 or 3, and B) 20–50% by weight of two or more compounds of the formula II

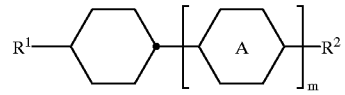

II in which $R^1$, $R^2$,

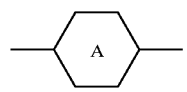

and m are as defined for the formula I.

2. A liquid-crystal display according to claim 1, wherein the liquid-crystalline medium comprises at least two compounds selected from those of the formulae Ia and Ib

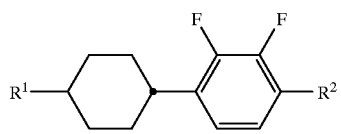

Ia

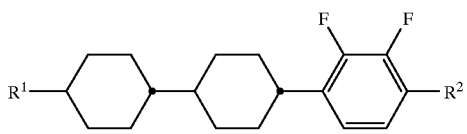

Ib in which $R^1$ and $R^2$ are as defined for the formula I.

3. A liquid-crystal display according to claim 1 wherein the liquid-crystalline medium comprises at least two compounds selected from those of the formulae IIa or IIc

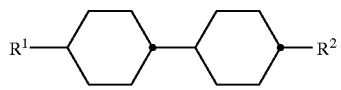

IIa

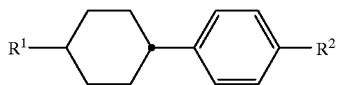

IIb

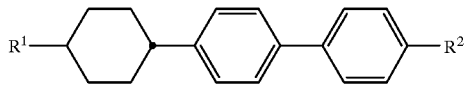

IIc in which $R^1$ and $R^2$ are as defined for the formula I.

4. A liquid-crystal display according to claim 1 wherein the liquid-crystalline medium additionally comprises one or more compounds of the formula IV

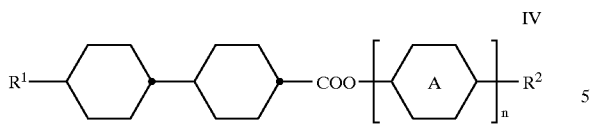

in which $R^1$, $R^2$ and

are as defined for the formula I, and n is 1 or 2.

5. A liquid-crystal display according to claim 1 which is capable of operation by active-matrix addressing based on the vertically alignment nematic effect.

6. A liquid-crystal display according to claim 1 which is capable of operation by active-matrix addressing based on the vertically aligned cholesteric effect.

7. A liquid-crystal display according to claim 1, wherein the liquid-crystalline medium has a nematic phase range of at least 60 K, a dielectric anisotropy, $\Delta\epsilon$, of from −0.5 to −5.0, a birefringence of from 0.04 to 0.15 and a rotational viscosity of 160 mPa·s or less.

8. A liquid-crystalline medium consisting essentially of:

A) 30–70% by weight of two or more compounds of the formula I

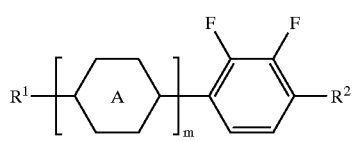

in which
   $R^1$ and $R^2$ are each, independently of one another, an alkyl or alkenyl radical having 1 to 15 carbon atoms which is unsubstituted, monosubstituted by CN or $CF_3$ or monosubstituted to perhalo-substituted by halogen, where, in addition, one or more $CH_2$ groups in these radicals are optionally independently of one another, replaced by —O—, —S—, —CO—, —CO—O—, —O—CO— or —OCO—O in such a way that —O— atoms are not linked to one another,

is a trans-1,4-cyclohexylene radical, in which one or more non-adjacent $CH_2$ groups are optionally replaced by —O— and/or —S—, or a 1,4-phenylene radical, in which one or two CH groups are optionally replaced by —N—, and m is 1, 2 or 3, B) 20–50% by weight of two or more compounds of the formula II

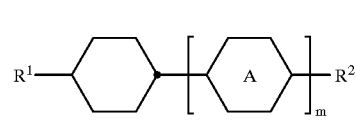

in which $R^1$, $R^2$,

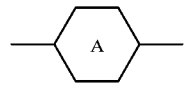

and m are as defined for the formula I, and
C) one or more compounds of the formula III

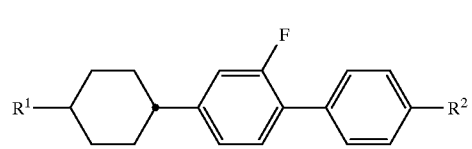

in which $R^1$ and $R^2$ are as defined for formula I.

9. The liquid-crystalline medium of claim 8, wherein the liquid-crystalline medium has a nematic phase range of at least 60 K, a dielectric anisotropy, $\Delta\epsilon$, of from −0.5 to −5.0, a birefringence of from 0.04 to 0.15 and a rotational viscosity of 160 mPa·s or less.

10. An electro-optical liquid-crystal display with active-matrix addressing, having a liquid-crystal layer with a homeotropic or tilted homeotropic alignment in the switched-off state and containing a liquid-crystalline medium of negative dielectric anisotropy, wherein the medium consists essentially of:

A) 30–70% by weight of two or more compounds of the formula I

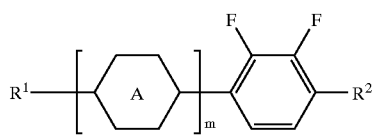

in which
   $R^1$ and $R^2$ are each, independently of one another, an alkyl or alkenyl radical having 1 to 15 carbon atoms which is unsubstituted, monosubstituted by CN or $CF_3$ or monosubstituted to perhalo-substituted by halogen, where, in addition, one or more $CH_2$ groups in these radicals are optionally independently of one another, replaced by —O—, —S—, —CO—, —CO—O—, —O—CO— or —OCO—O in such a way that —O— atoms are not linked to one another,

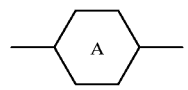

is a trans-1,4-cyclohexylene radical, in which one or more non-adjacent $CH_2$ groups are optionally replaced by —O— and/or —S—, or a 1,4-phenylene radical, in which one or two CH groups are optionally replaced by —N—, and m is 1, 2 or 3, B) 20–50% by weight of two or more compounds of the formula II

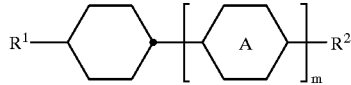

II in which $R^1$, $R^2$,

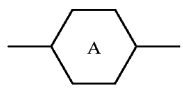

and m are as defined for the formula I, and

C) one or more compounds of the formula III

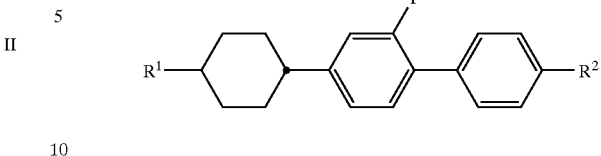

III in which $R^1$ and $R^2$ are as defined for the formula I.

11. A liquid-crystalline medium of claim 8, wherein the medium exhibits a maximum rotational viscosity of 160 mPa·s.

12. A display of claim 10, wherein the medium exhibits a maximum rotational viscosity of 160 mPa·s.

* * * * *